(12) United States Patent
Kuzma

(10) Patent No.: US 6,321,126 B1
(45) Date of Patent: Nov. 20, 2001

(54) IMPLANTABLE CONNECTOR

(75) Inventor: Janusz A. Kuzma, Englewood, CO (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/455,046

(22) Filed: Dec. 6, 1999

Related U.S. Application Data

(60) Provisional application No. 60/111,103, filed on Dec. 7, 1998.

(51) Int. Cl.$^7$ ........................................... A61N 1/375
(52) U.S. Cl. ........................... 607/137; 607/38; 439/909
(58) Field of Search ................................. 607/1, 2, 36–38, 607/116, 137, 55–57; 439/909

(56) References Cited

U.S. PATENT DOCUMENTS

| | | |
|---|---|---|
| 4,142,532 | 3/1979 | Ware . |
| 4,180,078 | 12/1979 | Anderson . |
| 4,284,085 | 8/1981 | Borkan et al. . |
| 4,411,277 | 10/1983 | Dickhudt . |
| 4,516,820 | 5/1985 | Kuzma . |
| 4,715,380 * | 12/1987 | Harris ....................................... 607/37 |
| 4,809,712 | 3/1989 | Kuzma . |
| 4,989,617 | 2/1991 | Memberg et al. . |
| 5,070,605 | 12/1991 | Daglow et al. . |
| 5,766,042 * | 6/1998 | Ries et al. ............................. 429/909 |

FOREIGN PATENT DOCUMENTS 9808554    3/1998    (WO) .

* cited by examiner

*Primary Examiner*—George R. Evanisko
(74) *Attorney, Agent, or Firm*—Bryant R. Gold

(57) ABSTRACT

An implantable connector electrically connects a multi-conductor lead (22) with a small-dimensioned implantable housing (102) of an implantable medical device, such as a cochlear stimulator. The implantable housing has electronic circuitry hermetically sealed therein. The implantable connector includes a header (10) formed along an edge of the implantable housing. The header has a cavity (11) formed therein with a first array of electrical contacts (12) embedded within a bottom surface of the cavity. The electrical contacts are electrically connected with the electronic circuitry through hermetic feedthrough terminals. The header further has a niche (15) and a channel (14) formed therein. A connector pad (20) is dimensioned to fit snugly within the cavity. A bottom surface of the connector pad has a second array of electrical contacts (21) formed therein. The second array of electrical contacts aligns with the first array of electrical contacts in the cavity when the pad is placed inside of the cavity. Electrical contact is established between the electrical contacts of the second array of electrical contacts and the electrical contacts of the first array when the connector pad is placed inside of the cavity. Each conductor within the multi-conductor lead (22) is electrically connected to at least one of the electrical contacts of the second array of electrical contacts. The lead (22) exits from the connector pad along one edge thereof so as to pass through the channel (14) formed within the header. A compressive spring (30) has a first end (33) secured within the niche (15) of the header (10), and has a second end locked to the header at the end of the header opposite the niche. The compressive spring (30) asserts a compressive force against the top surface of the connector pad as the connector pad is fitted within the cavity, thereby maintaining a secure electrical connection between the electrical contacts of the first and second arrays.

13 Claims, 2 Drawing Sheets

IMPLANTABLE CONNECTOR

This application claims the benefit of U.S. Provisional patent application Ser. No. 60/111,103, filed Dec. 7, 1998, which application is incorporated herein by reference.

BACKGROUND OF THE INVENTION

The present invention relates to implantable electronic and electrochemical medical devices and systems, and more particularly to a miniature implantable connector used with such devices and systems. Such connector is reliable, easy to manufacture, and provides multi-contact connections for use with limited-sized implantable stimulators, sensors, and the like.

Implantable electronic medical devices and systems have been in use for at least the past 20 years or more. One of the earliest implantable medical devices to be implanted in a patient was the cardiac pacemaker. Other implantable electronic devices have included neurostimulators, i.e., electrical stimulators designed to stimulate nerves or other tissue, sensors for sensing various physiological parameters or physical status of a patient, and other therapeutic-delivery devices, e.g., pumps for delivering controlled amounts of medication. In more recent years, the tiny implantable cochlear stimulator has been developed to allow patients who are profoundly deaf the ability to experience the sensation of hearing. Under development are other tiny implantable sensors and neurostimulators that will allow a patient who is a recipient of such sensors or stimulators the ability to walk, or to see, or to experience the use of other lost or impaired body functions.

Many of the implantable medical devices and systems described above require that at least one electrical lead be connected thereto in order for the device or system to perform its intended function. Such lead may terminate, e.g., in one or more electrodes designed to be in contact with body tissue. The cochlear stimulator, for example, has an electrode array adapted for insertion into the cochlea of the patient. Such electrode array typically employs a multiplicity of electrode contacts, e.g., 16–32 electrode contacts, each of which must be individually electrically connected to the electronic stimulation circuitry housed within an implantable housing. Other implantable electronic medical devices must be connected to a power source, or another sensor or other device, which requires an electrical lead, typically with at least two electrical conductors therein, for making the needed electrical connection between the devices or components of the system.

As the electronic medical devices and systems implanted in patients have become smaller and smaller, there has arisen a critical need for a reliable, easy-to-manufacture connector that allows a multi-conductor electrical lead to be detachably and reliably connected to the electronic circuitry hermetically sealed within a limited-sized implantable housing.

SUMMARY OF THE INVENTION

The present invention addresses the above and other needs by providing an easy-to-manufacture electrical connector formed in the housing of a limited-sized electronic device, e.g., an implantable neurostimulator, such as a cochlear implant, a pain-control device, pacemaker, or the like, that allows a multi-conductor electrical lead to be easily and reliably connected thereto. Advantageously, the invention herein described offers a simple, effective and small-dimensioned connector that facilitates a large number of separate electrical connections.

The connector of the invention includes a header, a connector pad and a compression spring. The header is made from a hard polymer, such as epoxy, and is typically formed on one side, or one segment, of the implantable case wherein the electronic circuitry associated with the implantable medical device is housed.

The header has a cavity with a flat bottom formed therein. An array of contacts are molded into the header so as to be flush with the bottom surface of the cavity. Each of the contacts are connected by wiring or other equivalent components, e.g., conductive traces, to hermetic feedthroughs that provide an electrical connection into the hermetically sealed chamber inside of the housing. In this manner, each of the contacts may thus be electrically connected to the electronic circuitry housed within the hermetically-sealed chamber.

The header also has two locking indentations, and a channel formed in the side walls that surround the cavity. The locking indentations are used to lock the compression spring against the connector pad when the connector pad is inserted into the cavity. The channel provides an exit opening through which a multi-conductor lead attached to the connector pad may exit when the connector pad is locked into the cavity. At an opposite end of cavity from the channel, a niche is formed for receiving one end of the compression spring. This niche securely holds one end of the compression spring while the other end is forced down over the connector pad and locked into place with the aid of the locking indentations.

The connector pad is molded from a silicone polymer into a flat paddle shape so as to have the same dimensions as the cavity of the header, thereby enabling the connector pad to be removably inserted, with a snug fit, within the cavity. An array of electrical contacts is formed on a bottom surface of the connector pad. This array of contacts matches with the array of contacts formed in the bottom of the cavity so that when the pad is inserted into the cavity, each contact of the connector pad may make electrical contact with at least one contact of the array of contacts formed in the bottom of the cavity. The contacts formed in the connector pad are electrically connected to conductors within a lead, which lead exists from a side of the connector pad at one end of thereof.

The compression spring is preferably made from a springy and biocompatible metal, such as Titanium Alloy 6AL-4V. It is permanently shaped to a radius R so that, unlocked, one end tends to lift or pull away from the connector pad while the other end remains engaged in the niche at one end of the header. The end of the spring the niche end has a locking bracket formed into a U-shape and is equipped with locking teeth that are adapted to engage the locking indentations formed in the sides of the connector header.

The connector is assembled by first placing the connector pad within the cavity of the header so that its contacts physically contact the header contacts formed in the array at the bottom of the cavity and so that the lead resides in the channel formed in the side of the header. One end of the compression spring is then inserted into the header niche, while the other end of the compression spring is pushed down until the teeth of the locking bracket engage and lock with the locking indentations formed in the side of the header. Once thus locked, a uniform compression force is applied to the surface of the connector pad, thereby compressibly forcing the electrical contacts formed on the bottom side of the connector pad firmly against the contacts within the cavity of the header. Alternative locking mechanisms may also be used to secure one end of the spring to the header, e.g., a screw or equivalent fastening element.

The connector may be opened by using a metal tool, like a screwdriver, to disengage the locking teeth of the compression spring from the indentations formed in the side of the header.

In an alternative embodiment, the header and its cavity are curved so as to form one segment around the periphery of an otherwise round or circular-shaped implantable housing. In such instance, the connector pad is also curved so as to fit in the curved cavity. The compressive spring, for such embodiment, may be formed to be straight, and as it is forced to assume the same curvature as the connector pad, a uniform compressive force is applied against the connector pad to hold it firmly in place within the cavity.

It is thus one feature of the present invention to provide a limited-sized, implantable, multi-conductor connector that may be used to detachably secure a multi-conductor lead to an implantable medical device.

It is another feature of the invention to provide such a connector that is sufficiently small to be used with an implantable cochlear stimulator or other small-sized implantable electronic device.

It is still another feature of the invention to allow a multi-conductor lead having a multiplicity of electrical conductors therein, e.g., a 8–32 conductors, to be electrically and detachably connected with electronic circuitry hermetically sealed within a limited-sized implantable medical device.

It is yet an additional feature of the invention to provide a multi-contact electrical connector for use along the edge of a disk-shaped or circular-shaped implantable housing that allows a multi-conductor lead to be detachably connected with the housing so that the lead exits tangentially from the housing, thereby facilitating implantation of the housing and lead into a relatively shallow pocket formed under the skin of its recipient.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
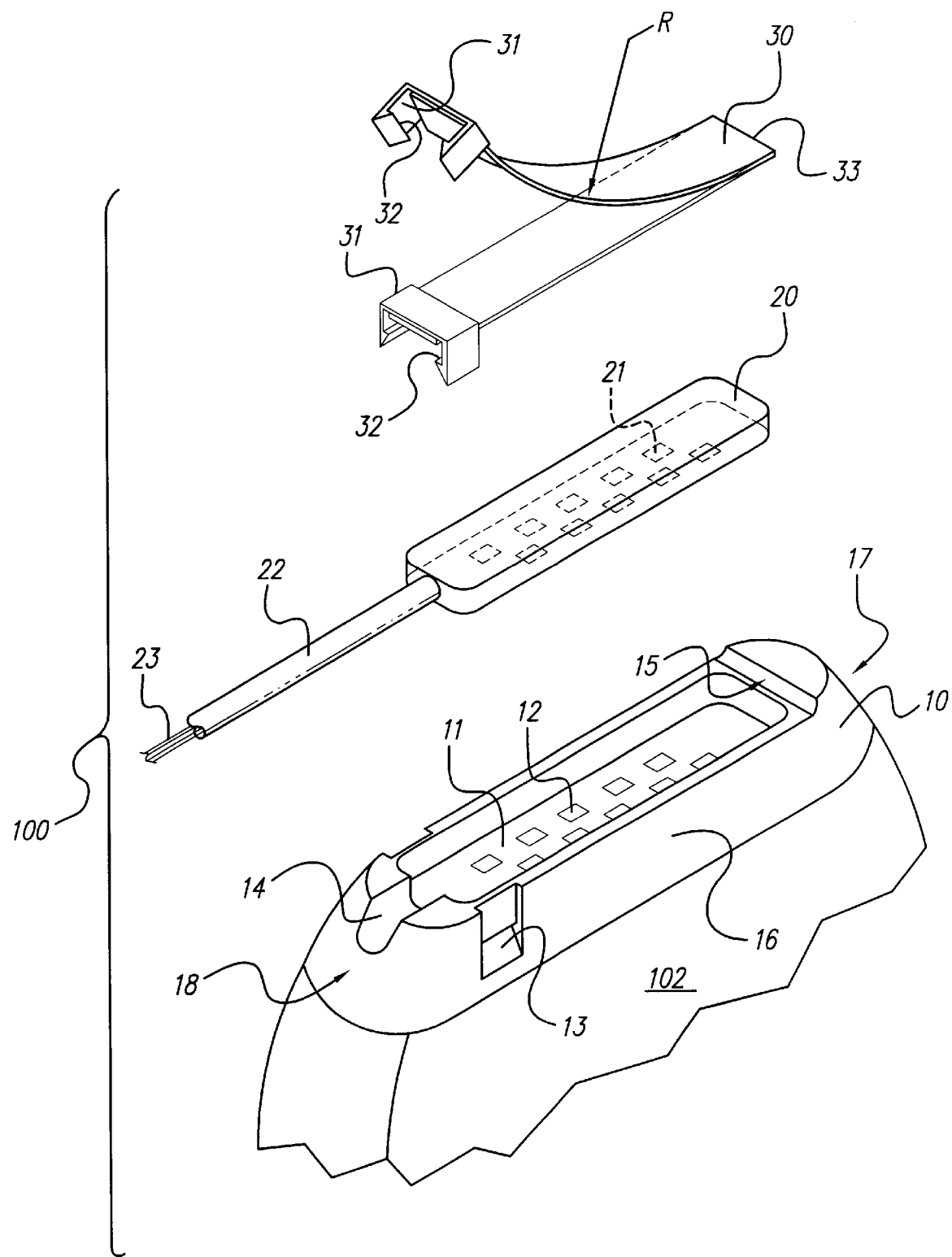
FIG. 1 is an exploded perspective view of one embodiment of an implantable medical device made in accordance with the present invention.

Turning first to FIG. 1, a preferred embodiment of a multi-contact connector 100 made in accordance with the present invention is depicted in an exploded perspective view. The connector 100 is designed to be used with an implantable device 102, which implantable device 102 has electronic circuitry hermetically sealed therein. The implantable device 102 may comprise any of many different types of muscle, tissue or neuro stimulators, e.g., a pacemaker, a cochlear stimulator, a pain-control stimulator, a brain stimulator, a bladder stimulator, and the like.

As seen in FIG. 1, the connector includes three main components: a header 10, a connector pad 20, and a compression spring 30. The header 10 is mounted to the edge of the implantable device 102, and is made from a hard polymer, such as epoxy. A cavity 11 is formed within the header 10. The cavity 11 has a flat bottom. An array of electrical contacts 12 are molded into the header so as to be exposed at and flush with the flat bottom of the cavity 11. The contacts 12 are electrically connected by wiring, or other conductive elements, to electrical feedthroughs that provide electrical connection with electronic circuitry housed within the hermetically-sealed device 102.

As further seen in FIG. 1, the cavity 11 formed in the header 10 is surrounded by header side walls 16 and a first end wall 17, and a second end wall 18. A niche 15 is formed near the top of the first end wall 17 and is adapted to receive a first end 33 of the compression spring 30. Two locking indentations 13 are formed in the side walls 16 near the second end wall 18 of the header. These locking indentations 13 are adapted to receive locking teeth 32 of a locking bracket 31 formed in or attached to a second end of the spring 30. A channel 14 is also formed in the second end wall 18 of the header 10. The channel 14 receives a multi-conductor lead 22 attached to the connector pad 20 when the connector pad 20 is inserted into the cavity 11.

The connector pad 20 is molded from silicone polymer in a paddle shape so as to fit snugly within the cavity 11. A sealing ridge, or O-ring, may be used as necessary, around the periphery of the pad 20. An array of contacts 21 is formed on the bottom surface of the pad 20. As necessary, these contacts 21 may protrude a slight amount from the bottom of the pad 20 to assure good electrical contact with the contacts 12 embedded in the bottom of the cavity 11 in the event such contacts 12 end up being slightly below the bottom surface of the cavity. Each contact of the array of contacts 21 is positioned within its array so as to match or be aligned with at least one corresponding contact 12 of the array of contacts formed within the header cavity 11 when the pad 20 is inserted into the cavity 11. Each of the pad contacts 21 is electrically connected to at least one conductor within multi-conductor lead 22.

The compression spring 30 is made from a biocompatible metal such as Titanium Alloy 6AL-4V and is fabricated so as to have a permanent bias, e.g., a bias that tends to force it to curve upward at radius R. The end 33 of the spring 30 is adapted to be inserted into the niche 15 of the header 10. The other end of the spring 30 has a locking bracket 31 attached thereto or formed therein. Such locking bracket 31 is typically formed into a U-shape, and has locking teeth 32 formed at each tip of the U bracket.

In order to assemble and use the connector 100, the connector pad 20 is placed within the cavity 11 of the header 10 so that the electrical contacts 21 on the bottom surface of the pad 20 face and make contact with the electrical contacts 12 formed in the bottom surface of the cavity 11. The lead 22 is placed in the channel 14. The first end 33 of the spring 30 is placed within the niche 15 of header 10. The other end of the spring 30, i.e., the end containing the locking bracket 31, is pressed down until the teeth 32 engage with the locking indentations 13, thereby holding the spring firmly in place against the top side of the pad 20. This asserts and maintains a uniform compressive force against the back side of the connector pad 20 so as to force and maintain a firm contact between the electrical contacts 21 of the connector pad 20 and the corresponding electrical contacts 12 in the bottom of the cavity 11. In turn, this allows electrical contact to be established and maintained between the conductors 23 within the multi-conductor lead 22 and the electronic circuitry that is hermetically-sealed within the housing 102.

Should it ever become necessary to detach the connector 100, all that need be done is to release the locking teeth 32 from the locking indentations 13, thereby allowing the spring 30 to pop open, and the pad 20 to be removed from the cavity 11. Such release can be performed with a suitable tool, such as a screwdriver, by simply forcing the teeth 32 away from the indentations 13.

Figure 2:
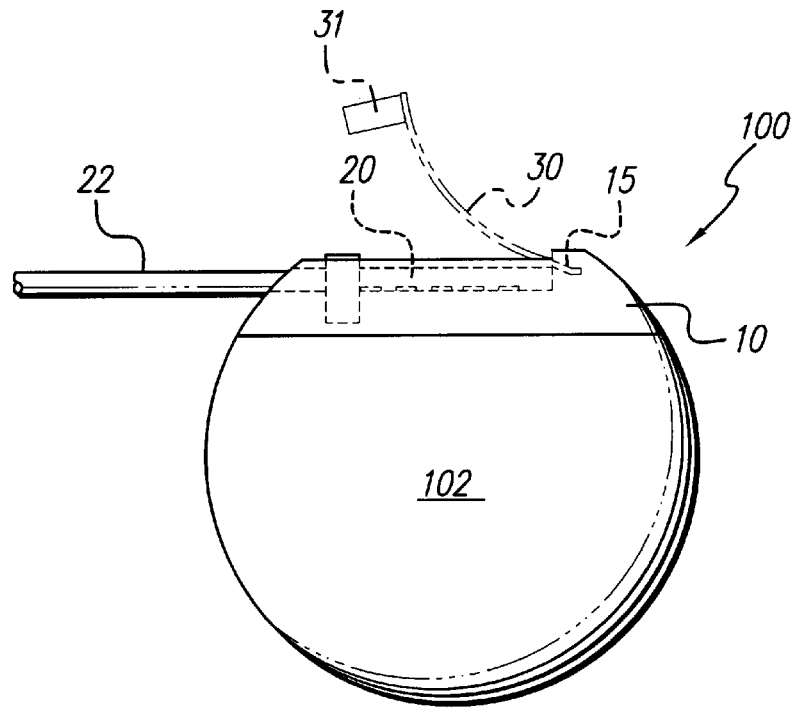
FIG. 2 shows a side view of the assembled connector of FIG. 1.

Referring next to FIG. 2, a schematic side view of the connector 100 of FIG. 1 is shown with the connector 100 fully assembled in its working position. FIG. 2 is particularly helpful for teaching a preferred orientation and shape of the niche 15 that is formed within the header 10. As seen in FIG. 2, the niche 15 comprises a slot that enters into the header 10 at an angle, and has a slight bend at its end.

Figure 3:
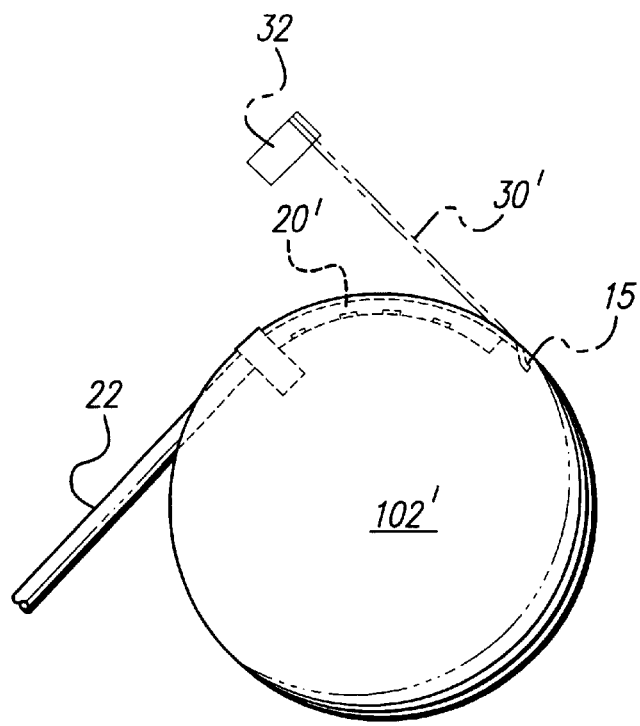
FIG. 3 illustrates a side view of an alternative embodiment of the connector.

FIG. 3 illustrates a second embodiment of the invention. This second embodiment utilizes the same principles as the first embodiment shown in FIGS. 1 and 2 except that the shape of the header 10 and its cavity 11 are altered to accommodate placement of the header on a curved surface of a disk-shaped or rounded-shaped housing 102'. That is, as seen in FIG. 3, the header and its cavity may be curved so as to form one segment around the periphery of an otherwise round or circular-shaped implantable housing 102'. The connector pad 20' is also curved so as to fit in the curved cavity. The compressive spring 30', for such embodiment, may be formed to be straight, and when pushed and locked to assume the same curvature as the connector pad, a uniform compressive force is applied against the connector pad 20' to hold it firmly in place within the cavity.

It is noted that the locking bracket 31 may be replaced, as needed or desired, by other locking mechanisms, such as a screw (screwed into the header through a treaded hole), thereby holding the connector in its working position. Where a screw is used in this manner, the first end 33 of the spring 30 is preferably engaged with the header 10 on the same end of the cavity as the output of lead 22, i.e., the niche 15 is formed at the same end of the cavity as the channel 14, and the threaded hole is placed on the opposite end of the cavity.

One of the advantages offered by the connector described herein is that it can readily be fabricated and used with extremely small implantable devices, e.g., devices which may have a housing size that is on the order of 30–35 mm in diameter or less, with a thickness of no more than about 7 mm, e.g., 5 to 6 mm. Yet, even at such small dimensions, it is possible to utilize a relatively large number of contact pads within the cavity 10 and the pad 20, e.g., 4 to 32 contacts or more.

As described above, it is thus seen that the connector of the present invention provides a limited-sized, implantable, multi-conductor connector that may be used to detachably secure a multi-conductor lead to an implantable medical device.

It is a further seen that the connector provided by the invention is sufficiently small to allow it to be used with an implantable cochlear stimulator or other small-sized implantable electronic device. Moreover, it is seen that the connector allows a multi-conductor lead having a multiplicity of electrical conductors therein, e.g., a 4–32 conductors, to be electrically and detachably connected with electronic circuitry hermetically sealed within a limited-sized implantable medical device.

Additionally, it is seen that the invention provides a multi-contact electrical connector for use along the edge of a disk-shaped or circular-shaped implantable housing that allows a multi-conductor lead to be detachably connected with the housing so that the lead exits tangentially from the housing, thereby facilitating implantation of the housing and lead into a relatively shallow pocket formed under the skin of its recipient.

While the invention herein disclosed has been described by means of specific embodiments and applications thereof, numerous modifications and variations could be made thereto by those skilled in the art without departing from the scope of the invention set forth in the claims.

What is claimed is:

1. An implantable medical device comprising:
   a small-dimensioned implantable housing (102);
   electronic circuitry hermetically sealed inside the implantable housing;
   a header (10) attached along an edge of the implantable housing, the header having a cavity (11) formed therein with a first array of electrical contacts (12) formed within the header on a bottom surface of the cavity, the electrical contacts (12) being electrically connected with the electronic circuitry, the header having a niche (15) and a channel (14) formed therein;
   a connector pad (20) inserted to fit snugly within the cavity, a bottom surface of the connector pad having a second array of electrical contacts (21) formed therein, wherein the second array of electrical contacts align with the array of electrical contacts (12) in the cavity (11) when the pad (20) is placed inside of the cavity (11), whereby the electrical contacts of the pad (20) touch and make electrical contact with the electrical contacts of the cavity (11) when the connector pad (20) is placed inside of the cavity (11);
   a multi-conductor lead (22) having a multiplicity of conductors wherein each conductor within the multi-conductor lead (22) is electrically connected to at least one of the electrical contacts of the second array of electrical contacts, and further wherein the lead (22) exits from the connector pad (20) along one edge thereof so as to pass through the channel (14) formed within the header (10);
   a compressive spring (30) having a first end (33) secured within the niche (15) of the header (10) and having a second end that is attachable to the header at an end of the header opposite the niche, wherein the compressive spring (30), when the second end of the spring is attached to the header, asserts a compressive force against a top surface of the connector pad as the connector pad is fitted within the cavity to maintain a secure electrical connection between the electrical contacts of the first and second arrays of electrical contacts.

2. The implantable medical device of claim 1 wherein the bottom surface of the cavity and the bottom surface of the connector pad are substantially flat.

3. The implantable medical device of claim 1 wherein the bottom surface of the cavity and the bottom surface of the connector pad are curved.

4. The implantable medical device of claim 1 wherein the header includes at least one locking indentation near or at the end opposite the niche, and wherein the compressive spring includes a locking bracket (31) at the second end of the spring, wherein the locking bracket has at least one locking tooth (32) that locks to the locking indentation of the header to lock the second end of the compressive spring to the header.

5. The implantable medical device of claim 4 wherein the header includes two locking indentations near or at the end opposite the niche, and wherein the compressive spring includes a U-shaped locking bracket (31) at a second end thereof, wherein the locking bracket has locking teeth (32) that lock to the locking indentations of the header to lock the compressive spring to the header.

6. The implantable medical device of claim 1 further including a fastener secured to the header and compressive spring that locks the second end of the spring to the header.

7. The implantable medical device of claim 1 wherein the number of electrical contacts included within the first array of electrical contacts in the header and included within the second array of electrical contacts in the connector pad includes at least four.

8. The implantable medical device of claim 7 wherein the number of electrical contacts included within the first array of electrical contacts in the header and included within the second array of electrical contacts in the connector pad includes at least eight.

9. The implantable medical device of claim 7 wherein the number of electrical contacts included within the first array of electrical contacts in the header and included within the second array of electrical contacts in the connector pad includes at least sixteen.

10. The implantable medical device of claim 1 wherein the small-dimensioned implantable housing comprises an implantable cochlear stimulator.

11. The implantable medical device of claim 10 wherein the implantable cochlear stimulator has a diameter less than about 35 mm and a thickness less than about 7 mm.

12. The implantable medical device of claim 1 wherein the connector pad includes a peripheral sealing ridge.

13. An implantable medical device and detachable multi-conductor lead, comprising:

an implantable housing;

electronic circuitry hermetically sealed inside the implantable housing;

a header attached along an edge of the implantable housing, the header having an open cavity formed therein with a first array of electrical contacts formed within the header on a bottom surface of the cavity, wherein the electrical contacts are electrically connected to the electronic circuitry, and further wherein the header has a niche and a channel formed therein;

a connector pad adapted to fit snugly within the cavity, a bottom surface of the connector pad having a second array of electrical contacts formed therein, wherein the second array of electrical contacts align with the array of electrical contacts in the cavity when the pad is placed inside of the cavity, whereby the electrical contacts of the pad touch and make electrical contact with the electrical contacts of the cavity when the connector pad is placed inside of the cavity;

wherein the multi-conductor lead has a multiplicity of conductors embedded therein, wherein each conductor within the multi-conductor lead is electrically connected to at least one of the electrical contacts of the second array of electrical contacts, and further wherein, when the pad is placed inside of the cavity, the lead exits from the connector pad along one edge thereof so as to pass through the channel formed within the header;

a compressive spring having a first end secured within the niche of the header and having a second end attachable to the header at an end of the header opposite the niche;

wherein, when the second end of the compressive spring is attached to the header, the compressive spring asserts a compressive force against a top surface of the connector pad as the connector pad is fitted within the cavity, wherein the compressive force maintains a secure electrical connection between the electrical contacts of the first and second arrays of electrical contacts.

* * * * *